(12) United States Patent
Burkhart et al.

(10) Patent No.: US 9,107,676 B2
(45) Date of Patent: Aug. 18, 2015

(54) LATARJET INSTRUMENTATION AND METHOD

(75) Inventors: Stephen S. Burkhart, San Antonio, TX (US); Sven Lichtenberg, Heidelberg (DE); John A. Sodeika, Naples, FL (US); Donald K. Shuler, Naples, FL (US); Ian K. Lo, Calgary (CA)

(73) Assignee: Arthrex, Inc., Naples, FL (US)

( * ) Notice: Subject to any disclaimer, the term of this patent is extended or adjusted under 35 U.S.C. 154(b) by 339 days.

(21) Appl. No.: 13/564,782

(22) Filed: Aug. 2, 2012

(65) Prior Publication Data

US 2012/0296338 A1 Nov. 22, 2012

Related U.S. Application Data

(62) Division of application No. 12/489,290, filed on Jun. 22, 2009, now Pat. No. 8,257,359.

(60) Provisional application No. 61/168,139, filed on Apr. 9, 2009, provisional application No. 61/074,528, filed on Jun. 20, 2008.

(51) Int. Cl.
| | |
|---|---|
| *A61B 17/58* | (2006.01) |
| *A61B 17/16* | (2006.01) |
| *A61B 17/17* | (2006.01) |
| *A61B 17/88* | (2006.01) |
| *A61B 17/29* | (2006.01) |
| *A61B 19/00* | (2006.01) |

(52) U.S. Cl.
CPC ......... *A61B 17/1657* (2013.01); *A61B 17/1604* (2013.01); *A61B 17/1684* (2013.01); *A61B 17/1735* (2013.01); *A61B 17/1796* (2013.01); *A61B 17/8866* (2013.01); *A61B 2017/1778* (2013.01); *A61B 2017/2926* (2013.01); *A61B 2019/304* (2013.01); *A61B 2019/462* (2013.01)

(58) Field of Classification Search
CPC .. A61B 17/15; A61B 17/151; A61B 17/1604; A61B 17/1739; A61B 17/1796
USPC .................................. 606/79–85, 87, 96, 99
See application file for complete search history.

(56) References Cited

U.S. PATENT DOCUMENTS

| | | | | |
|---|---|---|---|---|
| 2,181,746 | A * | 11/1939 | Siebrandt | 606/96 |
| 5,409,490 | A * | 4/1995 | Ethridge | 606/80 |
| 5,643,272 | A | 7/1997 | Haines | |
| 5,697,933 | A | 12/1997 | Gundlapalli | |
| 6,174,311 | B1 * | 1/2001 | Branch et al. | 606/86 A |
| 7,527,631 | B2 | 5/2009 | Maroney | |

(Continued)

FOREIGN PATENT DOCUMENTS

| | | |
|---|---|---|
| EP | 1 034 744 A1 | 9/2000 |
| WO | WO 2008/015670 A2 | 2/2008 |

OTHER PUBLICATIONS

EP1034744A1 Translation, Aug. 19, 2014.*

*Primary Examiner* — Nicholas Woodall
(74) *Attorney, Agent, or Firm* — Dickstein Shapiro LLP

(57) ABSTRACT

Instrumentation for an open or arthroscopic Latarjet procedure that allows more control graft handling during the formation of the hole and proper positioning parallel to the articulating bone surface. The surgical instrumentation of the present invention includes an osteotome with a plurality of markings and a depth stop, a drill guide with jaws configured to securely engage an outer surface of the graft, and an offset guide to position the graft to the bone.

8 Claims, 17 Drawing Sheets

(56) References Cited

U.S. PATENT DOCUMENTS

| | | | |
|---|---|---|---|
| 8,617,219 B2 * | 12/2013 | Oren et al. | 606/279 |
| 2005/0090829 A1 * | 4/2005 | Martz et al. | 606/79 |
| 2006/0074426 A1 * | 4/2006 | Lieberman | 606/79 |
| 2006/0074429 A1 * | 4/2006 | Ralph et al. | 606/84 |
| 2009/0318977 A1 | 12/2009 | Di Giacomo | |
| 2010/0069974 A1 | 3/2010 | Oren | |

* cited by examiner

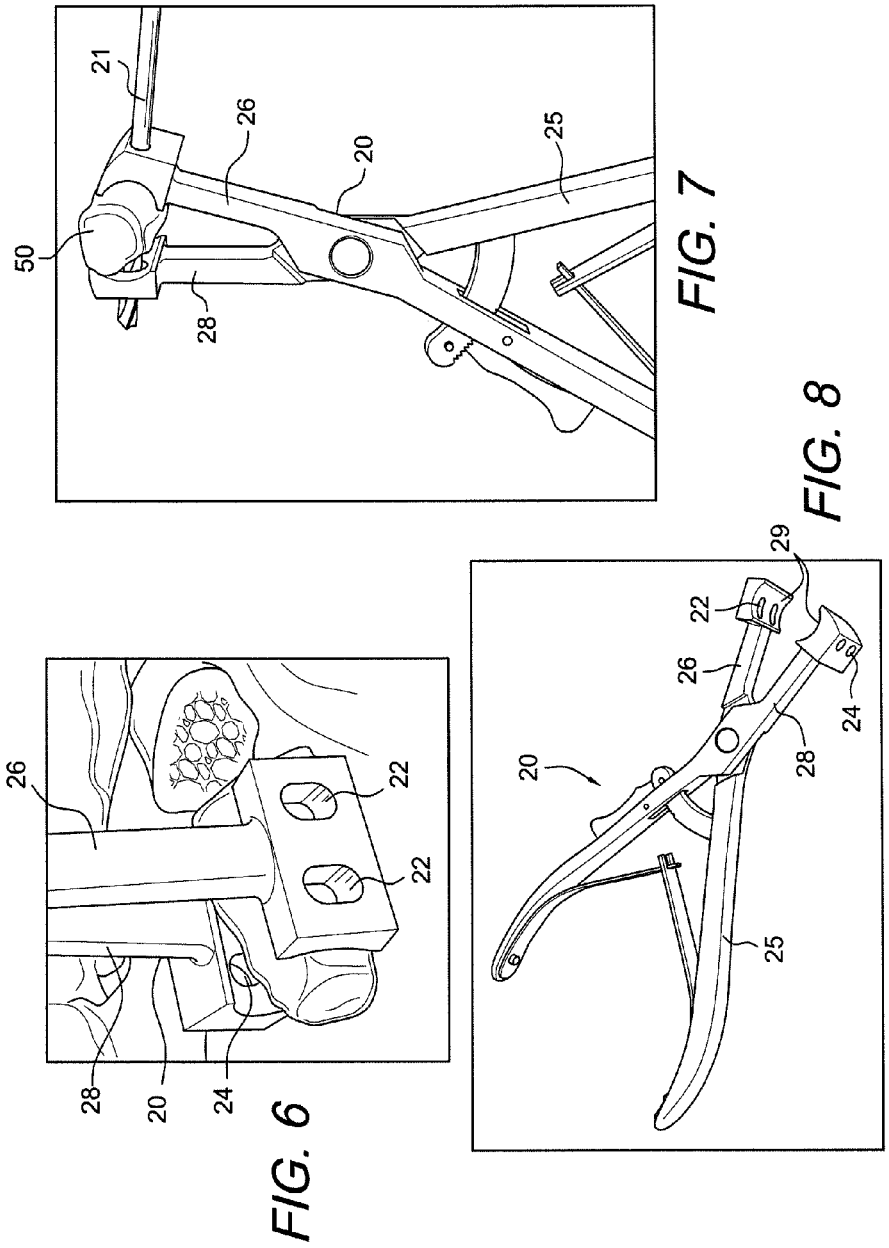

LATARJET INSTRUMENTATION AND METHOD

CROSS-REFERENCE TO RELATED APPLICATIONS

This is a divisional of U.S. application Ser. No. 12/489,290, filed Jun. 22, 2009 now U.S. Pat. No. 8,257,359, which claims the benefit of U.S. Provisional Application No. 61/168,139, filed Apr. 9, 2009, and of U.S. Provisional Application No. 61/074,528, filed Jun. 20, 2008, the entire disclosures of which are incorporated by reference herein.

BACKGROUND OF THE INVENTION

1. Field of the Invention

The present invention relates to osteotomies and, more specifically, to Latarjet instrumentation and methods of conducting a Latarjet procedure.

2. Description of the Related Art

The Latarjet procedure is known in the art and describes the coracoid bone block procedure. French surgeon Michel Latarjet first suggested that the horizontal limb of the coracoid process be fixed with a screw flush to the anteroinferior margin of the glenoid, making a horizontal incision through the fibers of the subscapularis. FIGS. 1 and 2 illustrate the attachment of the coracoid process 2 to the glenoid edge 4, to reduce instability during the Latarjet procedure. Although the Latarjet procedure has been constantly improved since 1954, specific instrumentation has not been designed to effectively address each step of the procedure. For example, surgeons are forced to improvise using general surgical instruments such as towel clamps to hold the coracoid process during cross hole drilling. This improvisation could result in non-parallel holes or, even worse, in breaking of the bone block which in turn could force abandonment of the procedure. Surgeons are also forced to "eyeball" the proper location of the coracoid graft, in an attempt to place it parallel to the articulating surface of the glenoid.

Accordingly, there is a need for improved instrumentation to be used during a Latarjet procedure, with reduced susceptibility to coracoid breakage, increased graft fixation, and correct alignment of the coracoid to the articulating surface of the glenoid.

SUMMARY OF THE INVENTION

The present invention provides improved instrumentation to be used during an open or arthroscopic procedure, that allows more control graft handling during the formation of the hole (drill hole formation) and proper positioning parallel to the articulating bone surface. The surgical instrumentation of the present invention includes, among others, an osteotome with a plurality of markings and a depth stop, a drill guide with jaws configured to securely engage an outer surface of the graft, and an offset guide to position the graft to the bone.

Other features and advantages of the present invention will become apparent from the following description of the invention, which refers to the accompanying drawings.

BRIEF DESCRIPTION OF THE DRAWINGS

FIGS. 3-16 illustrate various instruments of the present invention depicted at different stages of an open Latarjet procedure performed according to the present invention.

DETAILED DESCRIPTION OF THE PREFERRED EMBODIMENTS

Figure 1:
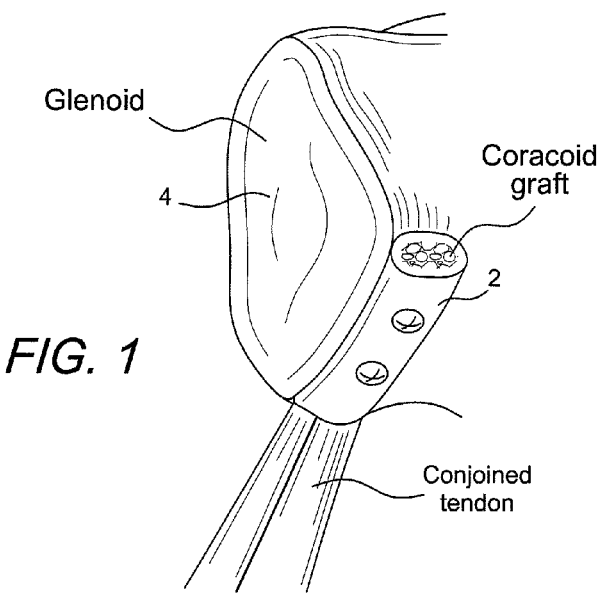
FIGS. 1 and 2 illustrate a perspective view and a cross-sectional view, respectively, of a coracoid process secured with screws during a conventional Latarjet procedure.
Figure 2:
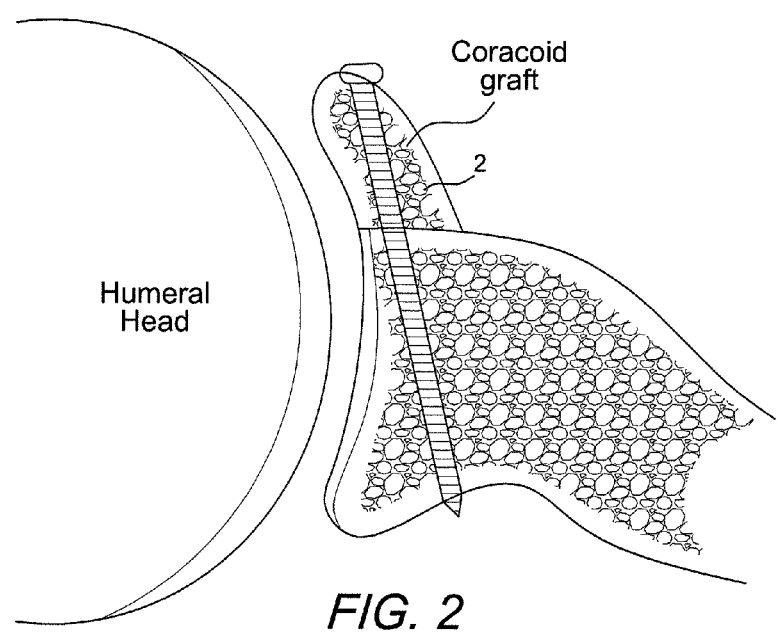

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The present invention provides improved instrumentation configured to be employed during a Latarjet procedure, with reduced susceptibility to coracoid breakage and increased graft positioning and fixation.

Referring now to the drawings, where like elements are designated by like reference numerals, FIGS. 3-16 illustrate various surgical instruments of the present invention employed in conjunction with an open Latarjet procedure. FIGS. 17-36 illustrate a sequence of steps of an exemplary open Latarjet procedure conducted by employing a system of the present invention including the plurality of surgical instruments of FIGS. 3-16. The unique surgical instrumentation of the present invention is configured to reduced susceptibility to coracoid breakage, increased graft positioning and fixation, and correct alignment of the coracoid to the articulating surface of the glenoid.

Figure 4:
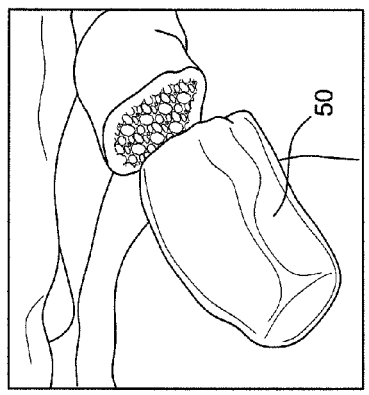
Figure 5:
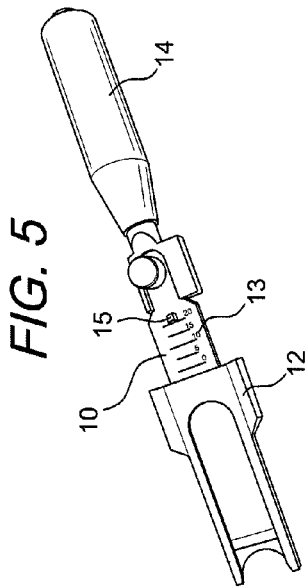
Figure 3:
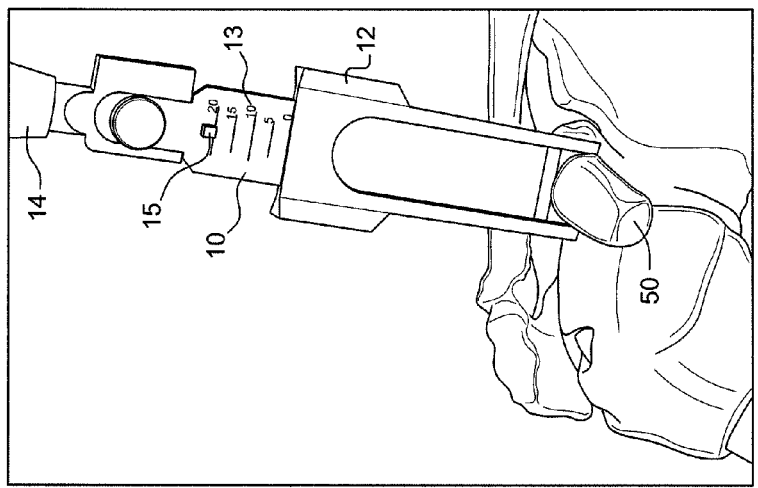

As shown in FIGS. 3-5, coracoid graft 50 is retrieved using a special osteotome 10 including a protective shield 12 (FIGS. 3 and 5) and an osteotome handle 14 (FIGS. 3 and 5). Osteotome blade 11 may be disposable and includes depth markings 13 and a hard stop 15 at about 20 mm. The osteotome shield protects the surrounding soft tissue, nerves and blood supply from inadvertent damage during the coracoid osteotomy.

Referring to FIGS. 6-8, the coracoid graft 50 is retrieved and secured with a grasping drill guide 20 (coracoid drill guide) that includes a ratcheting handle 25 and a pair of opposing jaws 26, 28 (a first jaw 26 and a second jaw 28) that are moveable with respect to each other. As shown in FIGS. 7 and 8, the most distal portion of each jaw 26, 28 is enlarged and provided with a curved inner surface 29 to conform to the outer surface and shape of the coracoid graft to be grasped by the jaws, to allow secure engagement of the graft by the opposing jaws (as shown in FIG. 7). As also shown in FIG. 8, one of the jaws (for example, jaw 26) is provided with a plurality of clearance slots 22, while the opposing jaw (for example, jaw 28) is provided with corresponding holes 24 (guide holes or drill holes 24). Clearance slots or openings 22 are larger than the drill holes 24, and are also elongated (as shown in FIG. 6, for example) to ensure that the end of the drill will pass therethrough without contacting the jaw.

Grasping drill guide 20 (shown in more detail in FIG. 8) is positioned on the graft 50 with clearance slots 22 adjacent to the surface of the coracoid that will eventually be in contact with the glenoid (as detailed below). Guide holes 24 of the grasping drill guide 20 allow a surgeon to drill two parallel holes (for example, two 4 mm holes) through the graft 50 approximately in the center of the graft.

Figure 10:
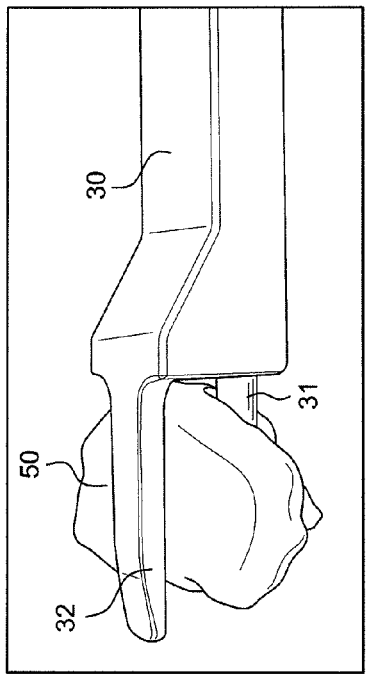
Figure 11:
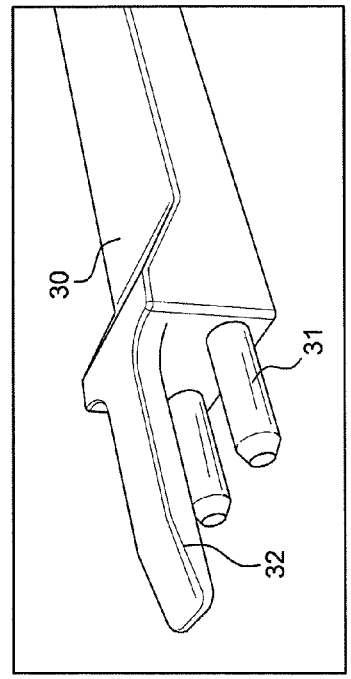
Figure 9:
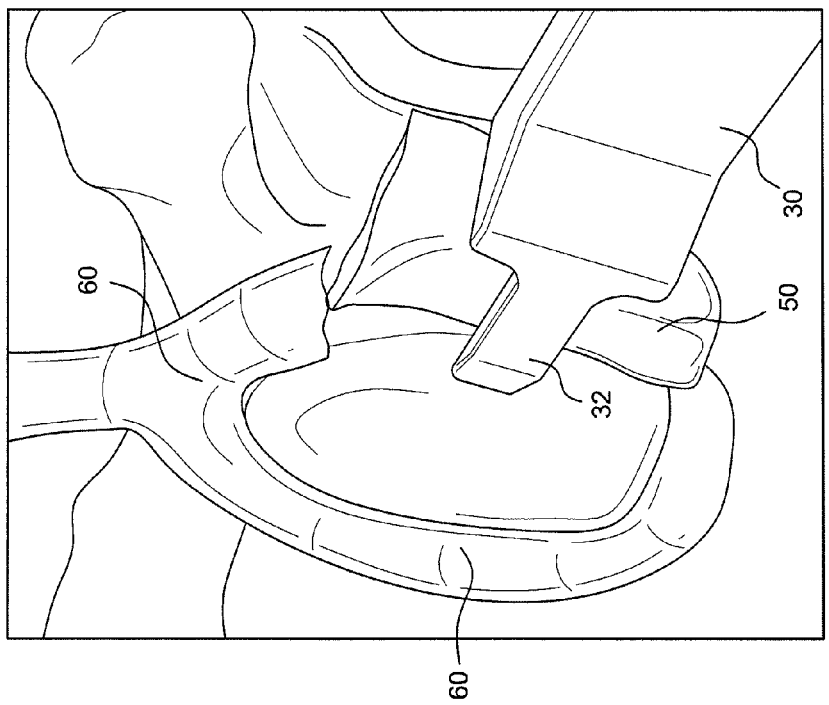

FIGS. 9-11 illustrate the attachment of the coracoid graft 50 to an offset guide 30 (glenoid drill guide 30) which is shown in more detail in FIGS. 10 and 11. In an exemplary embodiment only, the offset guide 30 is provided with a central extension 32 (in the shape of a flange, finger or protuberance, for example) to allow the extension 32 to sit on the surface of the glenoid and to securely hold the coracoid graft on the rim or edge of the glenoid, before the insertion of pins 33 (as explained below). According to an exemplary embodiment only, three different offset guides are provided at 4 mm, 6 mm and 8 mm based on the dimensions of the graft and bone (for example, based on the width of the coracoid graft and the width of the glenoid rim). FIGS. 9-11 illustrate an exemplary 6 mm offset guide. However, the invention contemplates any length of the extension or finger 32 (preferably, in increments of 2 mm).

In additional embodiments, the offset guide 30 (glenoid drill guide 30) may be configured without an "offset" at all (i.e., with no finger or extension that sits on the surface of the glenoid). In this embodiment, the offset guide is provided with the protruding finger or extension cut off, so that it resembles more a pitchfork. The offset guide of this exemplary embodiment would still hold the coracoid graft in the same manner (as the offset guide 30 with the extension 32), but allows the surgeon to freely position the graft anywhere on the anterior edge of the glenoid. In this manner, surgeons who follow the "French" Latarjet style (rather than the Latarjet procedure of the present invention) are able to position the graft more medially than the offset guide 30 (with the extension 32) allows.

Preferably, the offset guide 30 is cannulated (as shown in FIG. 11, for example), to allow insertion of guide pins through it directly (i.e., the guide pins are inserted directly through the cannulation(s) of the offset guide).

Figure 12:
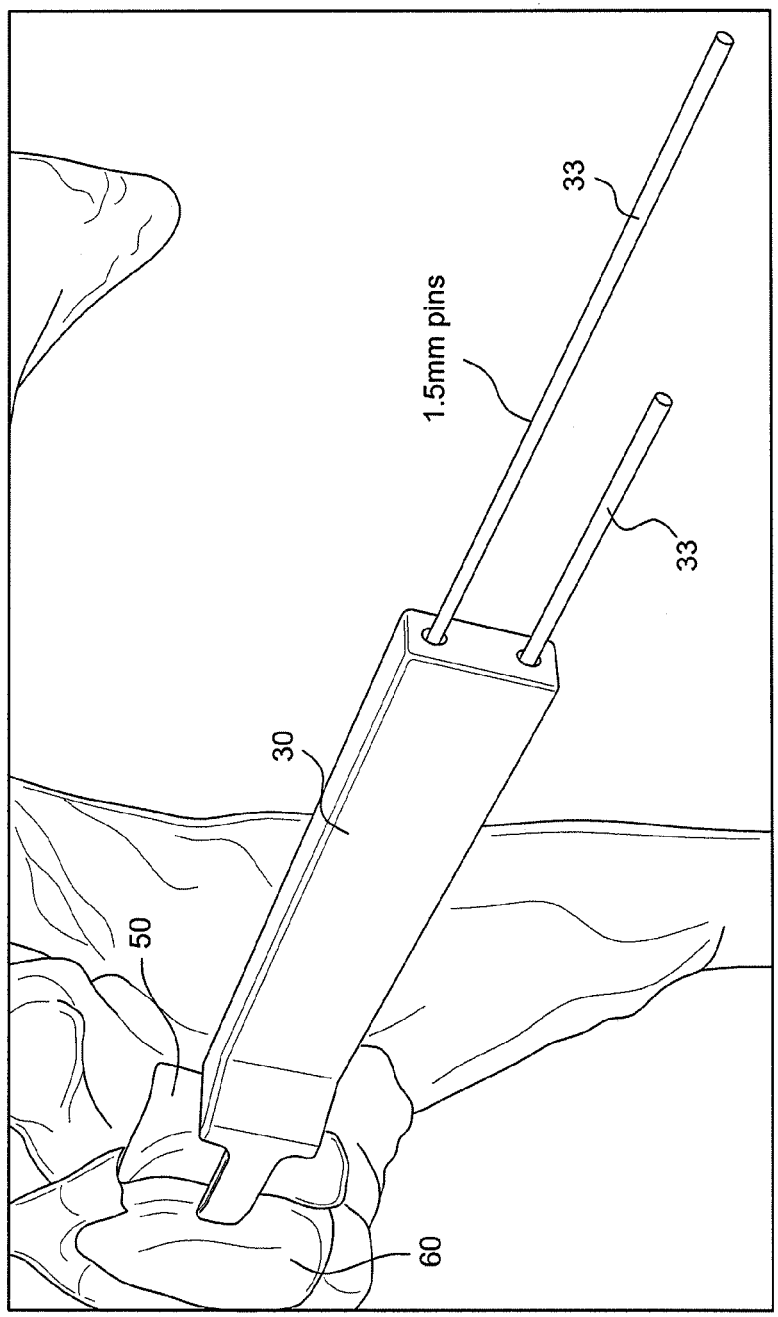

The coracoid graft 50 (attached to the offset guide 30) is subsequently positioned flush to the rim of glenoid 60 using the center flange 32 (extension 32), as shown in FIG. 9. Two parallel guide pins 33 (for example, two 1.5 mm guide pins 33) are drilled directly through the offset guide 30 and into the glenoid 60 (preferably conducted with fluoroscopy), as shown in FIG. 12. Preferably, pins 33 are of different length to allow equal depth of penetration without inadvertent contact from the drill chuck. The shorter pin is preferably drilled first.

Figure 14:
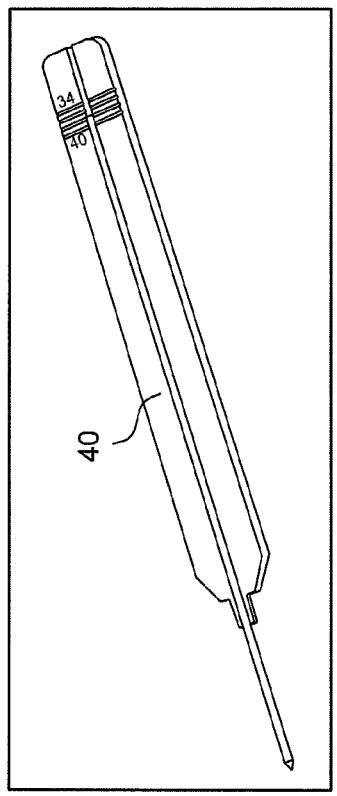
Figure 13:
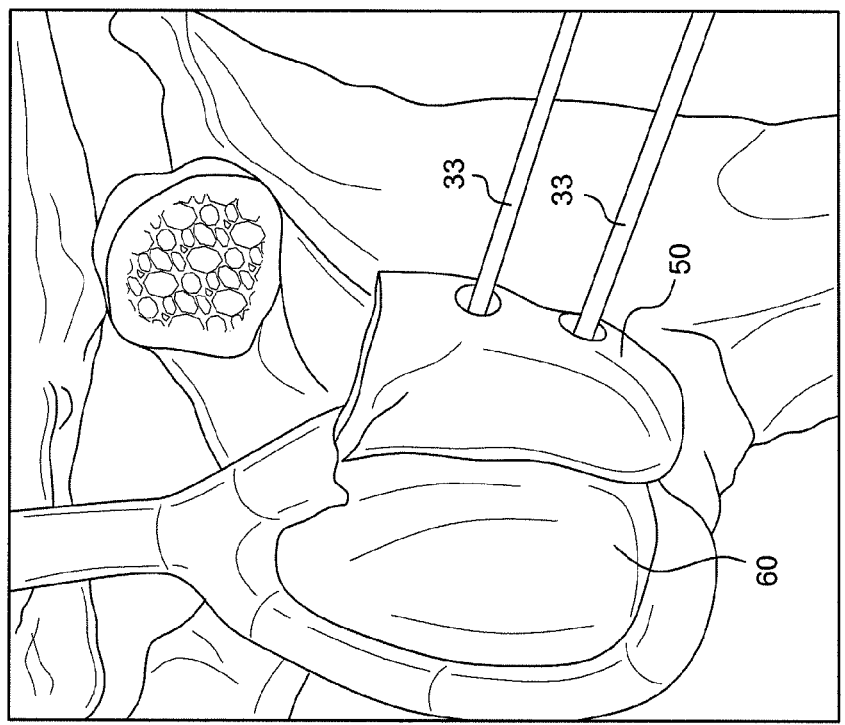

FIGS. 13 and 14 illustrate removal of the offset guide 30, leaving guide pins 33 in place. A depth gauge 40 (FIG. 14) may be employed to determine the optimum screw length, if desired.

Figure 16:
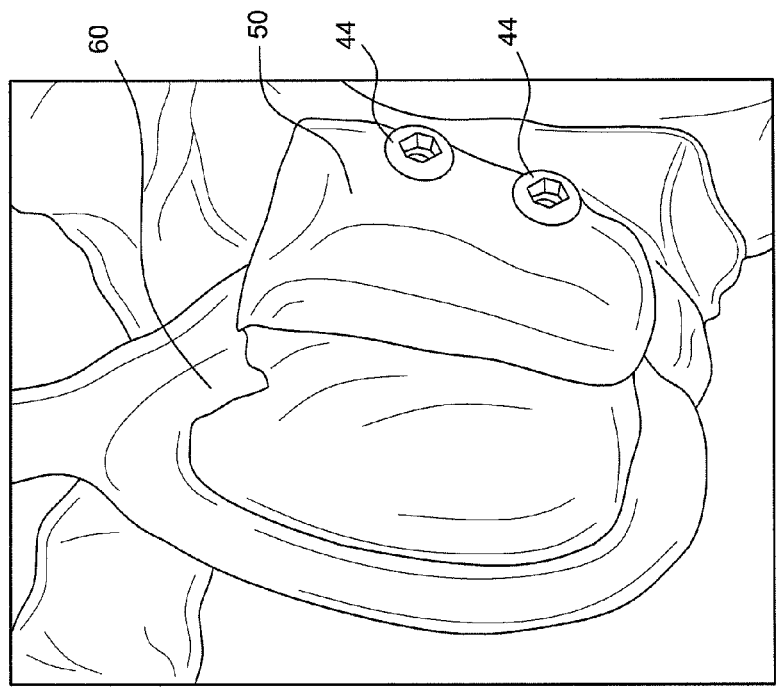
Figure 15:
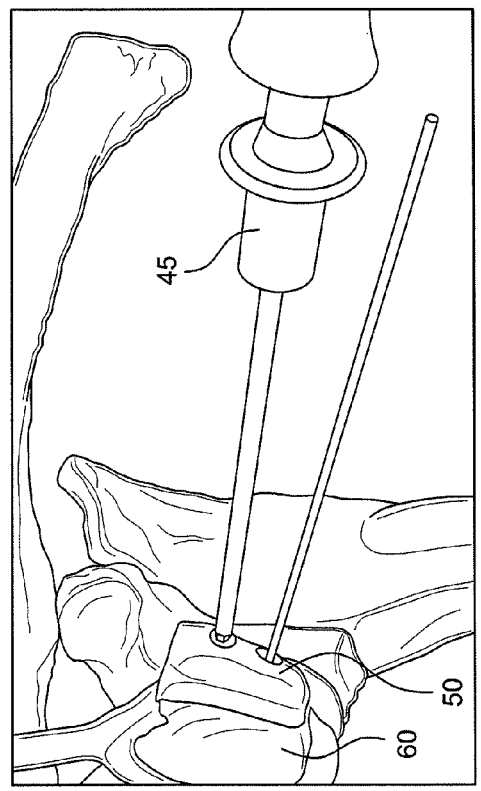

As shown in FIGS. 15 and 16, two fixation devices 44 (for example, two 3.75 mm self-tapping, cannulated titanium screws) are inserted using a driver 45 (for example, a 2.5 mm hex driver). The fixation devices may preferably comprise screws available in 30 to 42 mm lengths, in 2 mm increments.

In an alternative and exemplary only embodiment of the present invention, the offset guide 30 may be provided with only one post. This design allows use of the device through standard arthroscopic cannulas. As an example of how this instrument could be used, a surgeon could opt to use an illiac crest autograft (rather than a coracoid graft) to replace the missing glenoid bone. This illiac crest autograft could be shaped and sized and predrilled outside of the body. The graft would then be inserted into the shoulder. The single post offset guide would be arthroscopically inserted and mated with one of the predrilled graft holes. The guide would then be used to position the graft alongside the glenoid. A 1.5 mm guide pin would be drilled through the guide, which would then be repositioned onto the second predrilled hole, allowing the insertion of a second guide pin. The remainder of the technique would undergo as described above.

FIGS. 17-36 illustrate an exemplary sequence of steps of an open Latarjet procedure conducted by employing the plurality of surgical instruments described above with reference to FIGS. 3-16.

Figure 17:
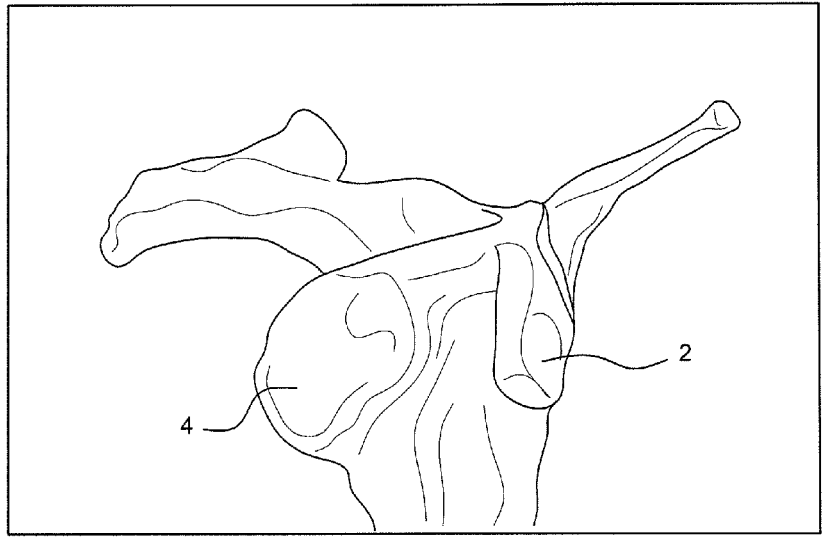
FIGS. 17-36 illustrate various steps of an open Latarjet procedure performed with the instrumentation of FIGS. 3-16 and according to an embodiment of the present invention.
Figure 18:
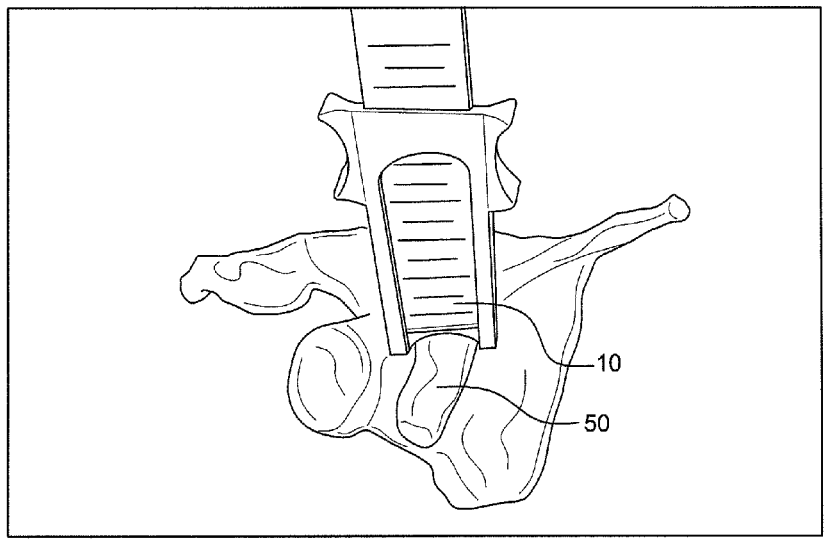
Figure 19:
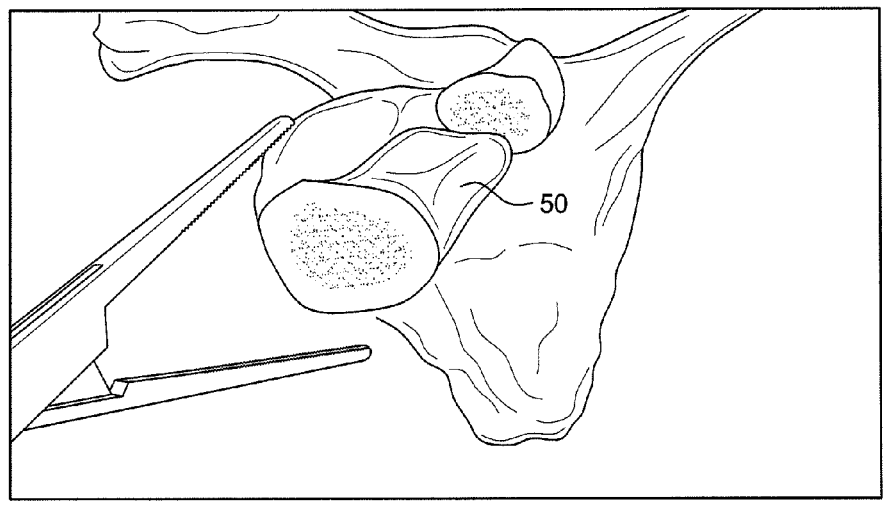

As shown in FIGS. 17 and 18, coracoid graft 50 is retrieved using the special osteotome 10 described above with reference to FIGS. 3-5. The shield 12 of the osteotome protects the surrounding soft tissue, nerves and blood supply from inadvertent damage during the coracoid osteotomy.

Figure 20:
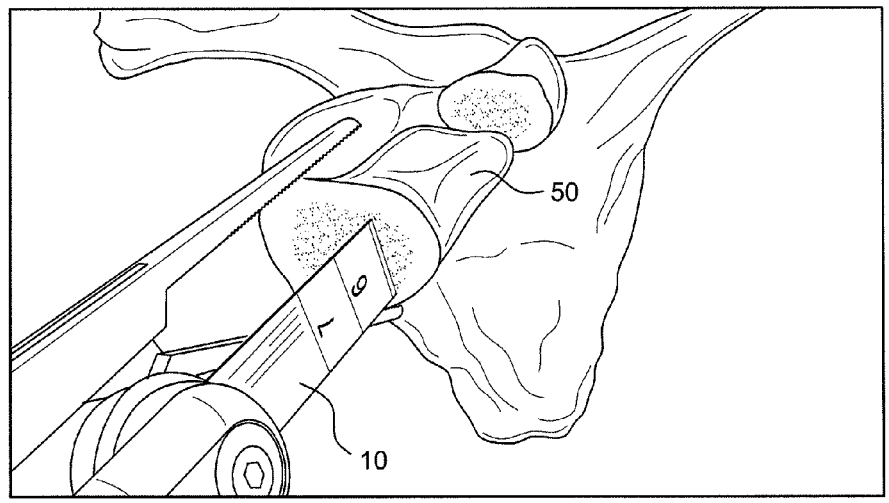
Figure 21:
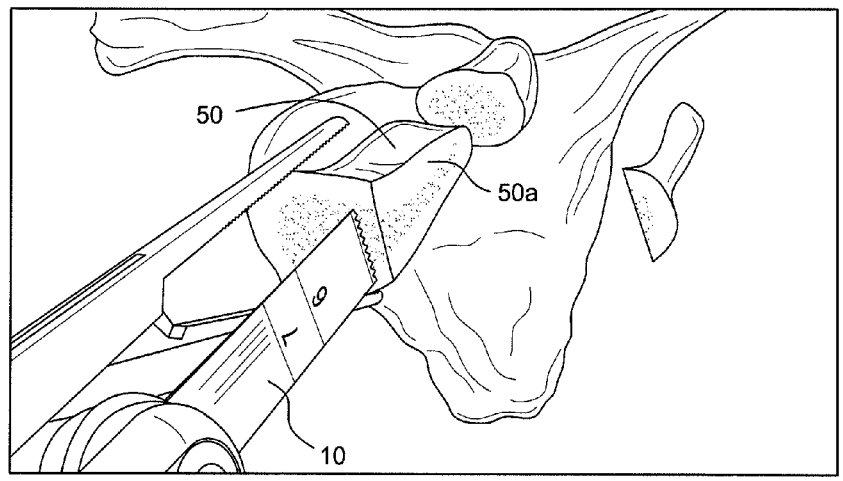
Figure 22:
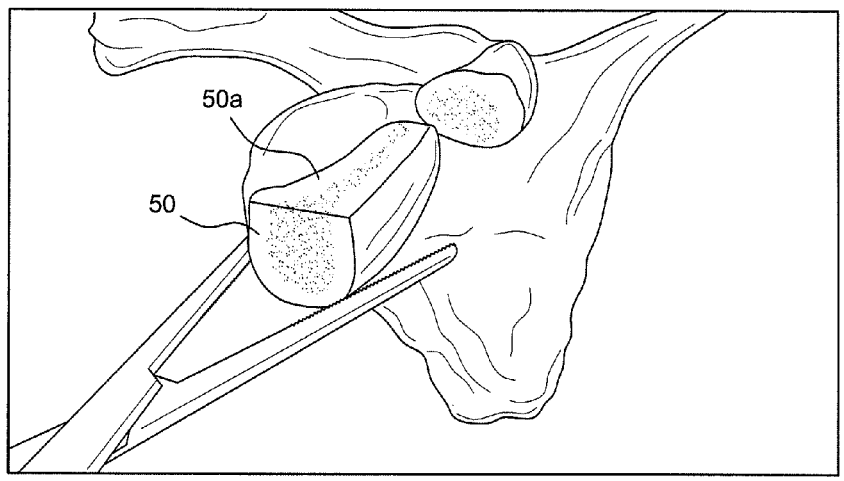
Figure 23:
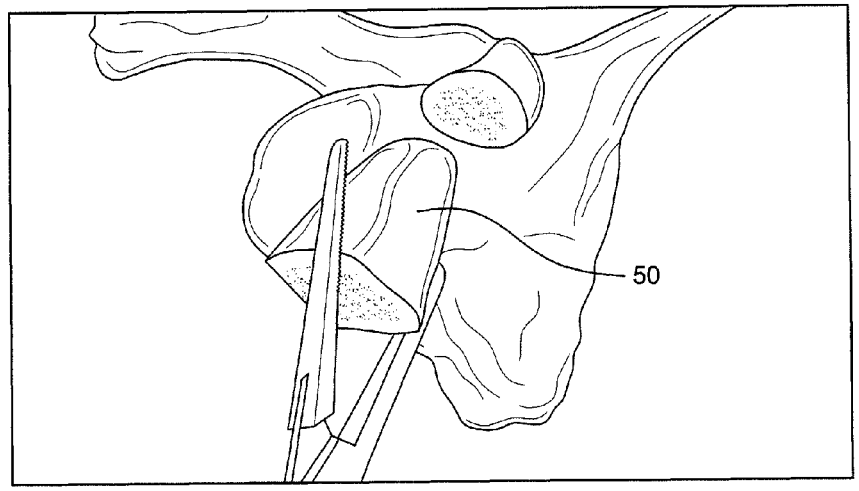

In an exemplary embodiment only, the coracoid graft 50 may be additionally shaped and sized (with the same osteotome or with a different cutting instrument, for example) to remove a lateral edge and to form a flat, cut surface 50a, as shown in FIGS. 20-22, for enhanced positioning alongside the glenoid. In this manner, the coracoid graft 50 is positioned so that the cut flat surface 50a abuts the rim of the glenoid (FIGS. 22 and 23).

Figure 24:
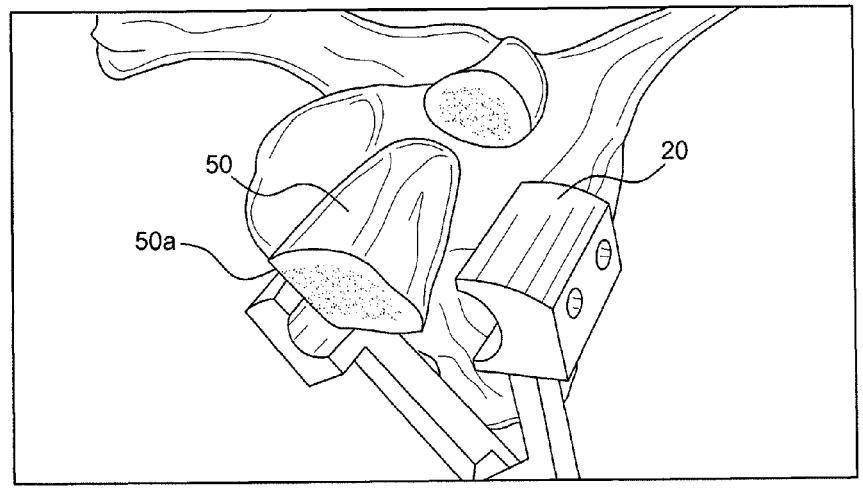
Figure 25:
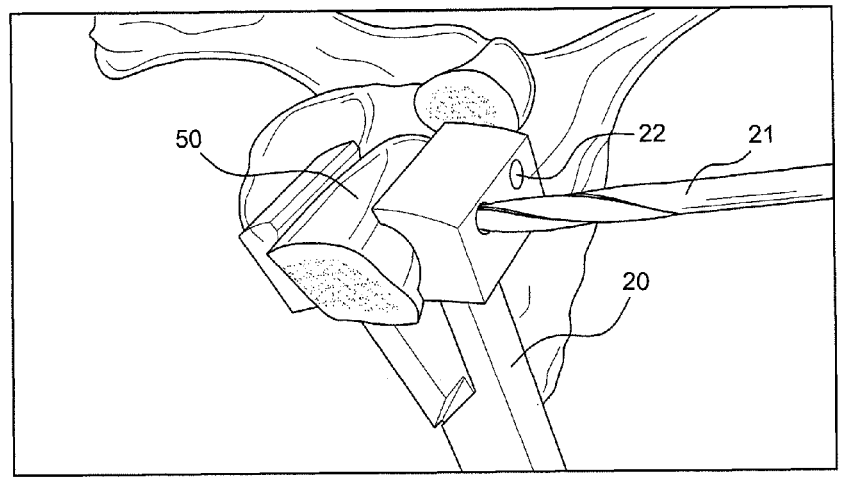
Figure 26:
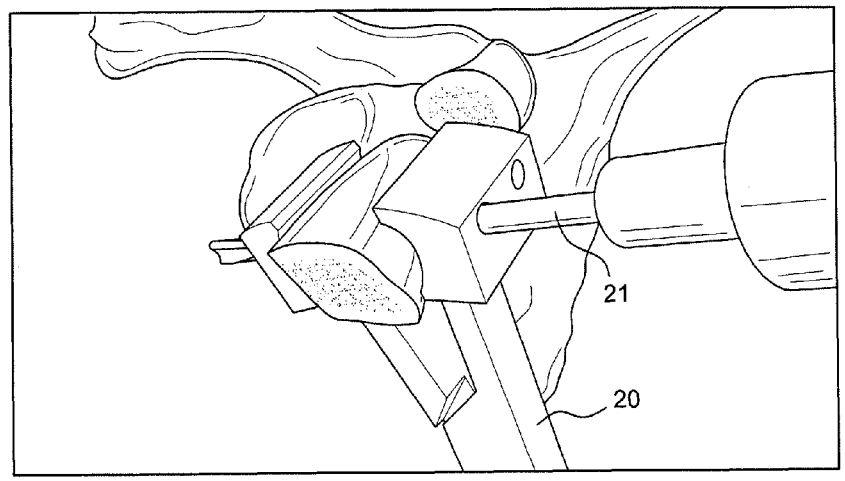
Figure 27:
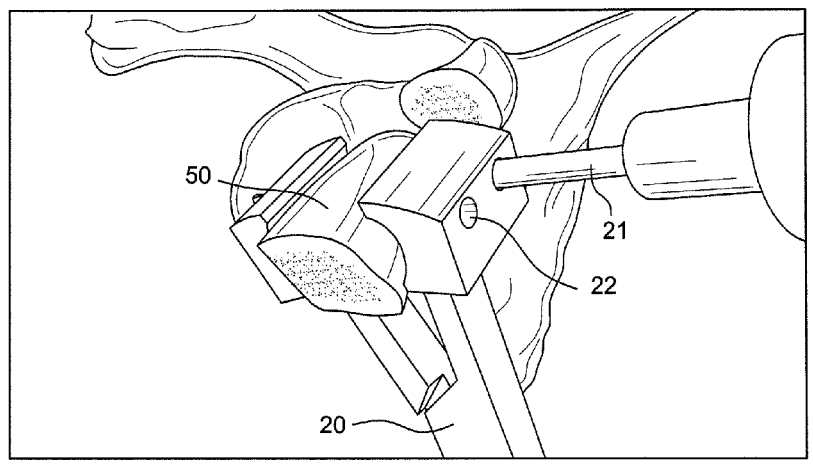
Figure 28:
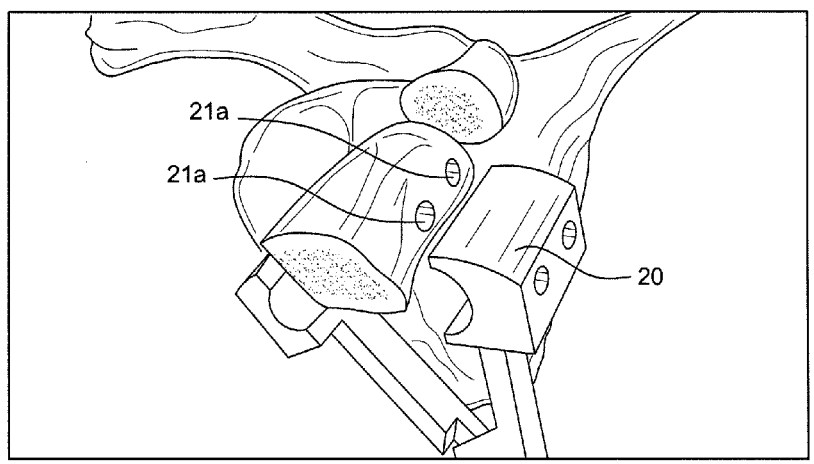

Once positioned on the glenoid rim, the coracoid graft 50 is secured within curved inner surfaces 29 of opposing jaws 26, 28 of the grasping drill guide 20 (coracoid guide), as shown in FIGS. 24 and 25.

FIGS. 25-28 illustrate the formation of holes 21a (FIG. 28) within the graft 50 by engaging drill 21 and by drilling through the clearance slots 22 and through the corresponding holes 24 (guide holes or drill holes 24) of jaws 26, 28. As detailed above, clearance slots or openings 22 are larger than the drill holes 24 (and may also be elongated, for example) to ensure that the end of the drill 21 will pass therethrough without contacting the jaw. Holes 21a are formed about parallel within graft 50, and are also formed approximately in the center of the graft. Holes 21 a may have various dimensions depending on the graft size and geometry (for example, about two 4 mm holes). In the exemplary embodiment illustrated with reference to FIGS. 25-28, holes 21a are formed sequentially; however, the invention is not limited to this embodiment and also contemplates the concurrent formation of holes 21a (as well as the formation of only one hole, depending on the number of cannulations of the offset guide 30).

Reference is now made to FIGS. 29-34. Subsequent to the formation of holes 21a, the grasping drill guide 20 (coracoid guide 20) is removed (FIG. 28), and the coracoid graft 50 is brought into contact with offset guide 30 (glenoid guide 30) which was described in more detail with reference to FIGS. 9-12.

Figure 29:
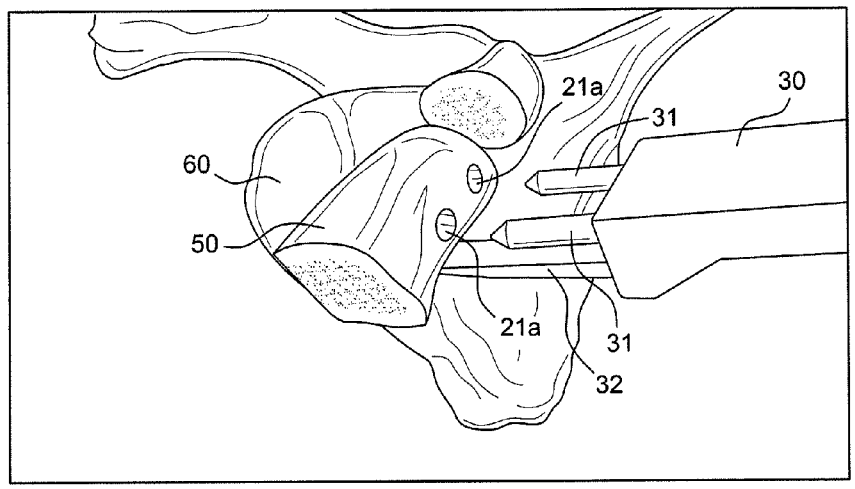
Figure 30:
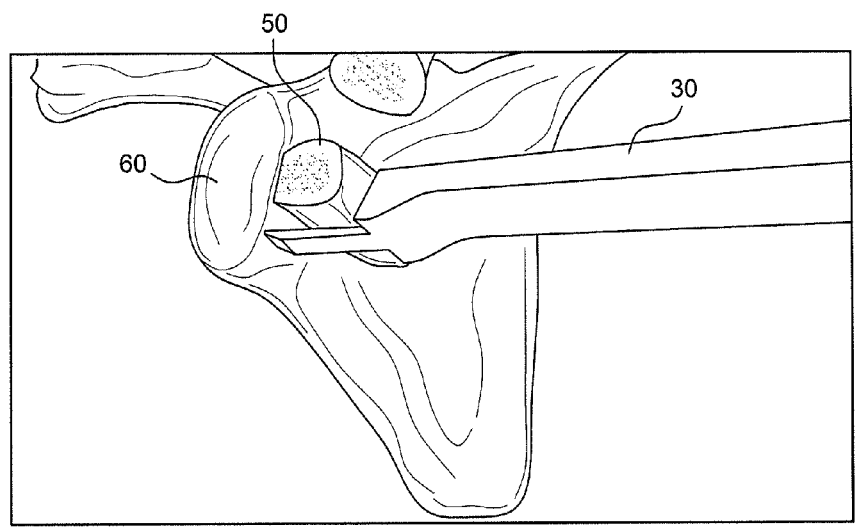
Figure 31:
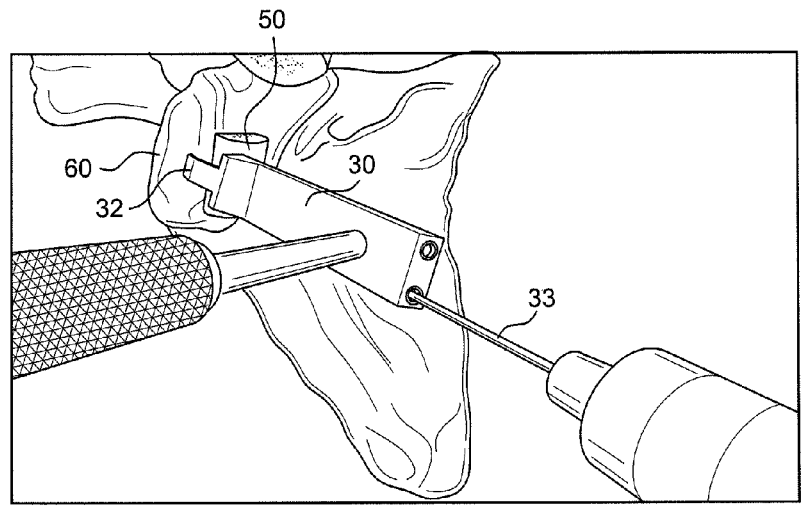
Figure 32:
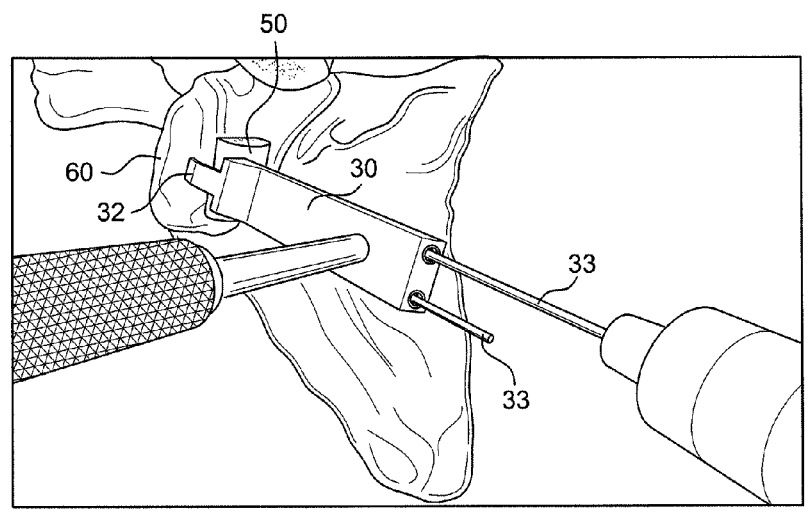

The coracoid graft 50 (attached to the offset guide 30) is subsequently positioned flush to the rim of glenoid 60 using the center flange 32, as shown in FIGS. 29 and 30. Two parallel guide pins 33 (for example, two 1.5 mm guide pins 33) are the inserted and drilled through cannulations 31 (FIG. 29) of the offset guide 30 and into the glenoid 60 (preferably conducted with fluoroscopy). FIGS. 31-34 illustrate the subsequent insertion of pins 33 through the offset guide 30. Preferably, pins 33 are of different length to allow equal depth of penetration without inadvertent contact from the drill chuck. The shorter pin is preferably drilled first.

Figure 33:
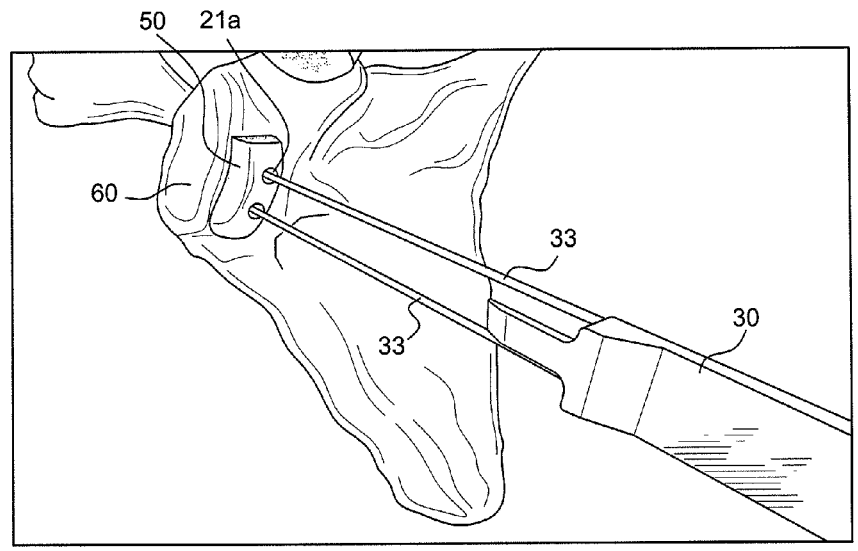
Figure 34:
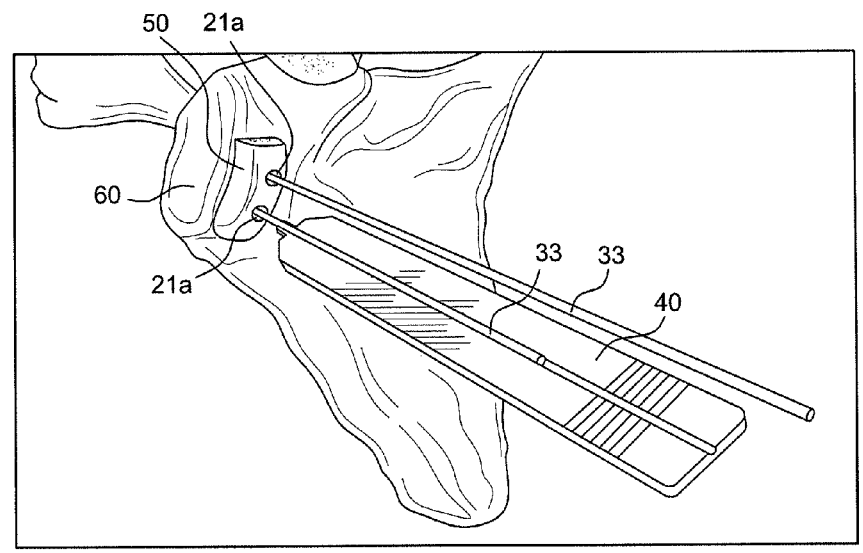
Figure 35:
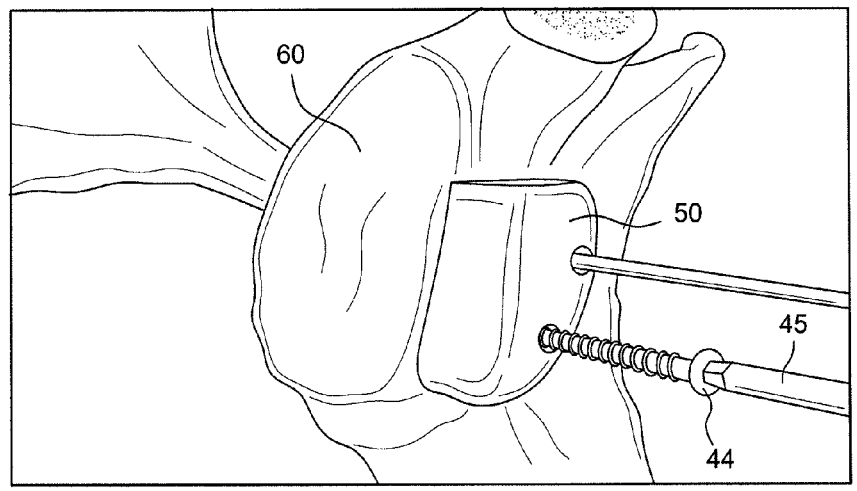
Figure 36:
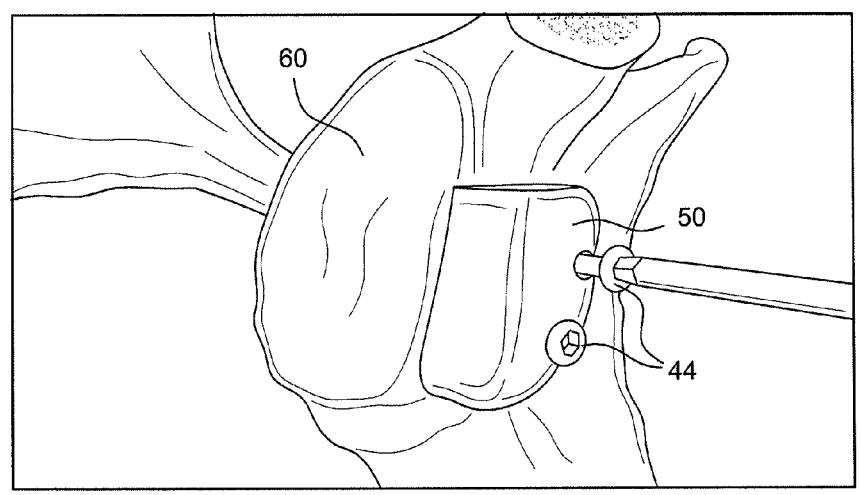

FIG. 33 illustrates the removal of the offset guide 30, leaving guide pins 33 in place. Depth gauge 40 (FIG. 34) may be employed to determine the optimum screw length, if desired. Two fixation devices 44 (for example, two 3.75 mm self-tapping, cannulated titanium screws) are inserted using driver 45, as shown in FIGS. 35 and 36, to complete the coracoid graft fixation. The fixation devices 44 may preferably comprise screws available in 30 to 42 mm lengths, in 2 mm increments.

Although the present invention has been described above with reference to a specific embodiment (i.e., a coracoid graft attached to the glenoid), the invention contemplates any attachment of a graft to bone, for example, any allograft or autograft attached to bone, or a graft from the illiac crest, or a tibial or scapular spine graft attached to any bone, among many others.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An instrument system for a Latarjet procedure, comprising:
    an osteotome comprising a blade with a plurality of markings and a depth stop at about 20 mm, the osteotome further comprising a protective shield to protect surrounding soft tissue, nerves and blood supply from inadvertent damage during coracoid osteotomy to obtain a coracoid graft;
    a drill guide comprising a pair of opposing jaws configured to securely engage the coracoid graft and to drill at least one hole through the coracoid graft, wherein the pair of opposing jaws comprise a first jaw and a second jaw, wherein one of the first and second jaws comprises a plurality of holes, and wherein the other of the first and second jaws comprises a plurality of slots, and wherein each of the first and second jaws comprises an enlarged distal tip with a curved inner surface which is complementary to an outer surface of the coracoid graft; and
    a glenoid drill guide configured to attach the coracoid graft to the glenoid rim and to drill at least one guide pin through the glenoid drill guide and into the glenoid, wherein the glenoid drill guide is cannulated to allow insertion directly therethrough of at least one guide pin.

2. The system of claim 1, wherein the blade of the osteotome is disposable.

3. The system of claim 1, further comprising:
    a depth gauge to determine a length of a fixation device to be secured to the coracoid graft; and
    at least one fixation device configured to attach the coracoid graft to the glenoid rim.

4. The system of claim 1, wherein the slots are larger than the holes.

5. The system of claim 1, wherein the drill guide comprises a ratchet handle.

6. The system of claim 1, wherein the glenoid drill guide is provided with an extension having a predetermined length.

7. The system of claim 6, wherein the predetermined length of the extension is one of a 4 mm, 6 mm, or 8 mm.

8. The system of claim 6, wherein the predetermined length of the glenoid drill guide is about equal to a width of the coracoid graft.

* * * * *